US012714683B2

(12) United States Patent
Wellendorph et al.

(10) Patent No.: US 12,714,683 B2
(45) Date of Patent: Aug. 25, 2026

(54) TREATMENT OF CNS DISORDERS WITH SLEEP DISTURBANCES

(71) Applicant: University of Copenhagen, Copenhagen K (DK)

(72) Inventors: Petrine Wellendorph, Kgs. Lyngby (DK); Birgitte Rahbek Kornum, Frederiksberg C (DK); Bente Frølund, Charlottenlund (DK)

(73) Assignee: UNIVERSITY OF COPENHAGEN, Copenhagen K (DK)

( * ) Notice: Subject to any disclaimer, the term of this patent is extended or adjusted under 35 U.S.C. 154(b) by 1025 days.

(21) Appl. No.: 17/621,044

(22) PCT Filed: Jun. 26, 2020

(86) PCT No.: PCT/DK2020/050197

§ 371 (c)(1),
(2) Date: Dec. 20, 2021

(87) PCT Pub. No.: WO2020/259787

PCT Pub. Date: Dec. 30, 2020

(65) Prior Publication Data

US 2022/0339131 A1 Oct. 27, 2022

(30) Foreign Application Priority Data

Jun. 28, 2019 (DK) .......................... PA 2019 70415

(51) Int. Cl.
*A61K 31/19* (2006.01)
*A61P 25/00* (2006.01)

(52) U.S. Cl.
CPC .............. *A61K 31/19* (2013.01); *A61P 25/00* (2018.01)

(58) Field of Classification Search
CPC ................................ A61K 31/19; A61P 25/00
USPC .......................................................... 514/572
See application file for complete search history.

(56) References Cited

U.S. PATENT DOCUMENTS

| | | | | |
|---|---|---|---|---|
| 8,772,306 | B1 * | 7/2014 | Eller | A61K 31/20 514/183 |
| 2007/0197650 | A1 | 8/2007 | Coop et al. | |
| 2011/0262442 | A1 * | 10/2011 | Hamilton | A61K 45/06 424/139.1 |
| 2017/0239197 | A1 | 8/2017 | Prous et al. | |

FOREIGN PATENT DOCUMENTS

| | | | |
|---|---|---|---|
| IT | MI991432 | A1 | 12/2000 |
| WO | 2001/005392 | A2 | 1/2001 |
| WO | 2019/149329 | A1 | 8/2019 |

OTHER PUBLICATIONS

Roden et al., Altered GABAA Receptor Subunit Expression and Pharmacology in Human Angelman Syndrome Cortex, Neuroscience Letters, 2010, vol. 483(3), pp. 167-172 (Year: 2010).*
Vogensen et al., New Synthesis and Tritium Labeling of a Selective Ligand for Studying High-Affinity γ Hydroxybutyrate (GHB) Binding Sites, Journal of Medicinal Chemistry, 2013, vol. 56, pp. 8201-8205 (Year: 2013).*
Wellendorph, P., Novel Cyclic y-Hydroxybutyrate (GHB) Analogs with High Affinity and Stereoselectivity of Binding to GHB Sites in Rat Brain, Journal of Pharmacology and Experimental Therapeutics, 315(1): 346-351, May 6, 2005.
Haack, M. et al., Sleep deficiency and chronic pain: potential underlying mechanisms and clinical implications, Neurophsychopharmacology, 45(1): 205-216, Jun. 17, 2019.
Qian, Y. et al., The role of CaMKII in neuropathic pain and fear memory in chronic constriction injury in rats, International Journal of Neuroscience, 129(2): 148-156, Dec. 5, 2018.
International Preliminary Report on Patentability for PCT/DK2020/050197, Dec. 28, 2021.
Carai et al., Role of GABA B receptors in the sedative/hypnotic effect of y-hydroxybutyric acid, European Journal of Pharmacology, 428: 315-321, 2001.
Jin et al., Effect of gamma-hydroxybutyric acid receptor on focal cerebral ischemia-reperfusion injury in rats, Acta Pharmaceutica Sinica, 42(8): 838-842, 2007.
Krall et al., Molecular Hybridization of potent and selective γ-Hydroxybutyric acid (GHB) ligands: Design, synthesis, binding studies, and molecular modeling of novel 3-Hydroxycyclopent-1-enecarboxylic acid (HOCPCA) and trans-γ-Hydroxycrotonic acid (T-HCA) analogs, Journal of Medicinal Chemistry, 60: 9022-9039, 2017.
Sindelar et al., Potential antidepressants and selective inhibitors of 5-Hydroxytryptamine re-uptake in the brain: Synthesis of several potential metabolites of moxifetin and of two A-ring fluorinated analogues, Collect. Czech. Chem. Commun., 56: 459-477, 1991.
Thiesen et al., In vitro and in vivo evidence for active brain uptake of the GHB analog HOCPCA by the monocarboxylate transporter subtype 1, Journal of Pharmacology and Experimental Therapeutics, 354: 166-174, Aug. 2015.

* cited by examiner

*Primary Examiner* — Jeffrey H Murray
*Assistant Examiner* — Rilla Marie Samsell
(74) *Attorney, Agent, or Firm* — DINSMORE & SHOHL LLP

(57) ABSTRACT

A compound for use in the treatment of CNS disorders with sleep disturbances e.g. narcolepsy or Angelman syndrome in a subject, wherein said compound is according to formula (I) or any isomer, tautomer, enantiomer, racemic form or deuterated form thereof, or a pharmaceutically acceptable salt thereof.

13 Claims, 5 Drawing Sheets

$^3$H-HOCPCA

TREATMENT OF CNS DISORDERS WITH SLEEP DISTURBANCES

FIELD OF THE INVENTION

The present invention relates to the fields of medicine, pharmacologically active compounds and pharmaceutical compositions comprising such compounds. Specifically, the invention relates to the treatment of CNS disorders with cognitive and sleep disturbances. This includes central hypersomnias such as narcolepsy, and neurodevelopmental disorders such as Angelman syndrome.

BACKGROUND

Sleep-wake regulation is tightly linked with synaptic function and plasticity, and recent findings have suggested that cycles of protein phosphorylation and dephosphorylation in neurons are a central molecular mechanism of sleep-wake regulation (Wang et al. Nature 2018, 558:435-439). It has so far been unknown whether compounds targeting CaMK2a could play a role in stabilising sleep disturbances or other CNS symptoms where there is an imbalance of neuronal activation and inhibition.

Narcolepsy is a chronic neurological disorder caused by the brain's inability to regulate sleep-wake cycles. It causes fragmented night sleep and excessive daytime sleepiness (EDS). At various times throughout the day, people with narcolepsy experience over-powering bouts of sleep. If the urge becomes overwhelming, they will fall asleep for periods lasting from a few seconds to several minutes but in rare cases some may remain asleep for an hour or longer.

Narcolepsy is a central hypersomnia. This group of disorders include idiopathic hypersomnia, recurrent hypersomnia such as Klein-Levin syndrome and narcolepsy including with cataplexy (narcolepsy type 1; narcolepsy-cataplexy syndrome; NRCLP1; narcolepsy with low hypocretin) and narcolepsy without cataplexy (narcolepsy type 2; narcolepsy with normal hypocretin).

All central hypersomnias are characterized by excessive daytime sleepiness (EDS), a persistent background feeling of sleepiness with a tendency to doze off at intervals throughout the day, often at inappropriate times. These are known as sleep attacks. It can lead to brain fog, poor concentration, decreased energy, memory lapses, exhaustion, and a depressed mood.

In addition to EDS, people with narcolepsy experience some or all of the typical symptoms of cataplexy (the sudden loss of voluntary muscle tone), abnormal rapid eye movement (REM) sleep, vivid hallucinations during sleep onset or upon awakening, and brief episodes of total paralysis at the beginning or end of sleep (called sleep paralysis). Cataplexy is specific for narcolepsy type 1, while the rest of the symptoms can occur in both narcolepsy type 1 and type 2.

In a typical sleep cycle, a person enters the early stage of sleep, followed by deeper sleep stages for 90 minutes where finally REM sleep occurs. For people with narcolepsy, REM sleep occurs within 15 minutes in the sleep cycle, and intermittently during the waking hours. It is in REM sleep that dreams and muscle paralysis occur.

Hallucinations are vivid, often frightening sensory hallucinations that occur while falling asleep (hypnogogic hallucinations), which could be caused by the blend of wakefulness and the dreaming that occurs with REM sleep.

Sleep paralysis is a brief inability to move or speak while falling asleep or waking up. These episodes can last from a few seconds to several minutes. After the episode ends, people rapidly recover their full capacity to move and speak.

Automatic behaviors can also occur. A person may fall asleep momentarily but continue doing the previous activity, such as driving, without being conscious.

Cataplexy is a sudden muscle weakness in the entire body or partial for instance in the face. Some people have only mild weakness, such as head or jaw drop, but some people completely collapse to the ground. These episodes are often triggered by strong emotions, such as surprise, laughter, or anger. The weakness is typically temporary, lasting 2 minutes or less, but can be longer in severe cases.

Narcolepsy can range in severity from mild to severe. In severe cases, it can negatively impact social activities, school, work, and overall health and well-being. A person with narcolepsy may fall asleep at any time, often without warning, for example while talking, standing or driving.

Symptoms tend to appear in the teenage years, or early twenties and thirties. Men and women are equally susceptible, and prevalence of narcolepsy is about 1 in 2,000 individuals.

Similar symptoms are shown also by individuals affected by Narcolepsy Due to Medical Condition (NDMC), a group of disorders also known as secondary or symptomatic narcolepsy. Examples of medical conditions causing narcolepsy symptoms including cataplexy are: tumors, ischemic stroke, sarcoidosis, arteriovenous malformations affecting the hypothalamus, multiple sclerosis plaques impairing the hypothalamus, paraneoplastic syndrome antt-Ma2 antibodies, Neimann-Pick type C disease or Coffin-Lowry syndrome. Examples of medical conditions commonly causing narcolepsy symptoms without cataplexy are: head trauma, myotonic dystrophy, Prader-Willi syndrome, Parkinson's disease or multisystem atrophy.

GHB is a naturally occurring γ-aminobutyric acid (GABA) metabolite and a neuromodulator that is present in micromolar concentrations in the mammalian brain. GHB (sodium oxybate) is used both clinically as a prescribed drug in narcolepsy, and it is abused as a recreational drug (e.g. Fantasy). GHB displays both low affinity (millimolar) binding to $GABA_B$ receptors and high affinity (nanomolar to micromolar) binding to a specific protein in neurons, which has recently been identified as CaMK2a (PCT/DK2019/050041). Mediated by $GABA_B$ receptors, one well-established pharmacological effect of GHB is a lowering of body temperature. By contrast, the neuro-physiological and -pharmacological effects related to the CaMK2a binding site are still unknown.

CaMK2a is one of the most abundant proteins in the postsynaptic density. It is a major regulator of synaptic signaling through its phosphorylation of ion channels and neuro-transmitter receptors and is intimately involved in synaptic plasticity, a process that occurs at postsynaptic densities, and thus higher brain functions such as cognitive processes. Due to its central role in regulating synaptic function, CaMK2a is involved in most neurological diseases and is a promising drug target, yet unexplored due to the unavailability of small-molecule brain-penetrant ligands with selectivity for the 2a subtype. GHB is highly efficacious in treating cataplexy and excessive daytime sleepiness in relation to narcolepsy. It is widely believed that this effect is due to the effects of GHB on $GABA_B$ receptors. The effect of GHB on sleep parameters are similar between wild type mice and $GABA_B$ receptor knock-out mice (Vienne et al. J Neurosci 2010, 30:14194-14204) and further a study shows that the $GABA_B$ receptor agonist baclofen also has efficacy on narcolepsy symptoms in a mouse model of narcolepsy type 1 (Black et al. J Neurosci 2014, 34:6485-6494). Compounds related to GHB may thus have efficacy in narcolepsy through effects on CaMK2a and/or $GABA_B$ receptors. This could be via down-stream effects on the $GABA_A$ receptor.

Angelman syndrome is a rare, chronic neurodevelopmental disorder which is caused by loss of function of the gene ubiquitin protein ligase E3A (UBE3A). The disorder affects 1 in 12-20,000 people and is initiated at birth. AS is characterized by intellectual disability, impaired motor coordination, epilepsy, sleep disturbances and behavioral abnormalities including autism spectrum disorder (ASD) features.

Wellendorph et al (J Pharmacol Exp Ther 2005, 315:346-351) discloses cyclic GHB analogues and their affinities to native binding sites.

Krall et al (J Med Chem 2019, 60:9022-9039) discloses a structure-affinity relationship-study for ligands targeting binding sites for the neuroactive compound GHB.

Thiesen et al (J Pharmacol Exp Ther 2015, 354:166-174) discloses facilitated brain up-take of 3-hydroxycyclopent-1-enecarboxylic acid (HOCPCA) by the monocarboxylate transporter 1 (MCT1), and demonstrates that MCT1 is an important brain entry site for this compound.

PCT/DK2019/050041 discloses that GHB analogues bind with high affinity to CaMK2a and that compounds targeting this kinase are useful for the treatment of brain injuries.

WO/2019/055369 discloses the use of gaboxadol in the treatment of narcolepsy. The $GABA_A$ receptor agonist gaboxadol has been in clinical development for a range of diseases in the 1980's and 1990's but patients with a history of drug abuse who received gaboxadol experienced an increase in psychiatric adverse events.

There is a need for effective and safe new treatment options for CNS disorders with sleep disturbances. There is also a need for new drug for the treatment of central hypersomnias including narcolepsy, which do not have the potential for abuse or which have a better pharmacokinetics as compared to e.g. sodium oxybate. Furthermore, there is a need for treatment options in neurodevelopmental disorders such as Angelman and Down syndromes for which no targeted treatment exists and in which cognitive and sleep disturbances are central. Thus, a specific option for treating sleep disturbances would be relevant for all neurodevelopmental disorders.

SUMMARY

The present inventors have found that a wide range of GHB analogues display binding to $Ca^{2+}$/calmodulin-dependent protein kinase 2a (CaMK2a), and thus compounds of Formula I holds promise for the treatment of CNS disorders with sleep disturbances such as central hypersomnias, exemplified by narcolepsy type 1, and neurodevelopment disorders involving CaMK2a dysfunction, exemplified by Angelman syndrome.

In its first aspect, the present invention provides a compound for use in the treatment of a CNS disorder with sleep disturbances in a subject, wherein said compound is according to formula I (formula I)

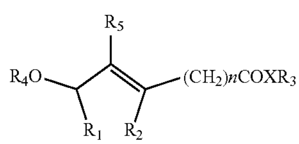

wherein when $R_5$ is H, and $R_1$ and $R_2$ form a ring system, then said compound is selected from the following compounds of formula II or formula IV (formula II)

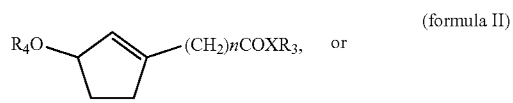

or (formula IV)

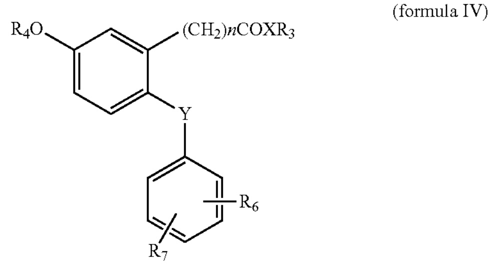

wherein n is 0 or 1;

X is selected from O or NH

Y is NH, O, S, $CH_2$ $R_3$ is selected from H, linear or branched $C_1$-$C_6$-alkyl including -Me, -Et, —Pr, -iPr, —Bu, -tBu, -iBu, pentyl, neopentyl, hexyl, branched henxyl, -benzyl, polyethylenglycolyl (PEG), or a group such as

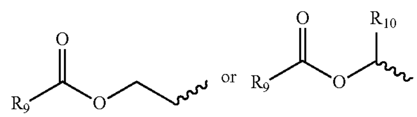

wherein $R_9$ and $R_{10}$ independently of each other are selected from linear or branched $C_1$-$C_6$ including -Me, -Et, —Pr, -iPr, -Bu, -iBu, -tBu, pentyl, neopentyl, hexyl; notably $R_{10}$ is selected from H, -Me, -Et, -iPr;

$R_4$ is selected from H, —C(═O)—$C_1$-$C_6$-alkyl, wherein alkyl is linear or branched including —C(═O)-Me, —C(═O)-Et, —C(═O)—Pr, —C(═O)-iPr, —C(═O)—Bu, —C(═O)-tBu; —C(═O)-benzyl, polyethylenglycolyl (PEG), or a groups such as

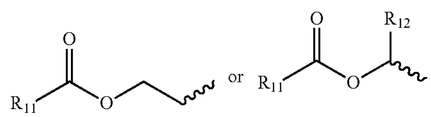

wherein $R_{11}$ and $R_{12}$ independently of each other are selected from linear or branched $C_1$-$C_6$-alkyl including -Me, -Et, —Pr, -iPr, -Bu, -iBu, -tBu, pentyl, neopentyl, hexyl; notably $R_{12}$ is selected from H, -Me, -Et, -iPr; -iBu $R_6$, and $R_7$ are independently from each other selected from H, F, Cl, Br, I, aryl, straight or branched $C_{1-8}$ alkyl, —$CH_2(CH_2)_p$-aryl, —CH═CH-aryl, $NH_2$, $NO_2$, OH, SH, straight or branched —O—$C_{1-8}$ alkyl, straight or branched —S—$C_{1-8}$ alkyl, straight or branched —NH—$C_{1-8}$ alkyl, —O-aryl, —S-aryl, —NH-aryl, wherein aryl includes aryl having one or more heteroatoms selected from O, N or S, and wherein p is 0 or 1; and $C_{1-8}$ alkyl includes Me, Et, Pr, Bu, pentyl, hexyl, heptyl, octyl-alkyl being linear or branched or when $R_2$ is H, and $R_1$ and $R_5$ form a ring system, then said compound has formula III (formula III)

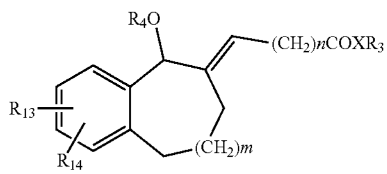

wherein n is 0 or 1;

X is O or NH m is 0 or 1;

$R_3$ is selected from H, linear or branched $C_1$-$C_6$-alkyl including -Me, -Et, —Pr, -iPr, -Bu, -tBu, -iBu, pentyl, isopentyl, neopentyl, hexyl, branched hexyl, -benzyl, polyethylenglycolyl (PEG), or a group such as

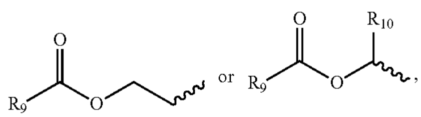

wherein $R_9$ and $R_{10}$ independently of each other are selected from linear or branched $C_1$-$C_6$-alkyl, wherein alkyl is linear or branched including -Me, -Et, —Pr, -iPr, -Bu, -iBu, -tBu, pentyl, neopentyl, hexyl; notably $R_{10}$ is selected from H, -Me, -Et, -iPr;

$R_4$ is selected from H, —C(═O)—$C_1$-$C_6$-alkyl including —C(═O)-Me, —C(═O)-Et, —C(═O)—Pr, —C(═O)-iPr, —C(═O)—Bu, —C(═O)-tBu; —C(═O)-benzyl, polyethylenglycolyl (PEG), or a groups such as

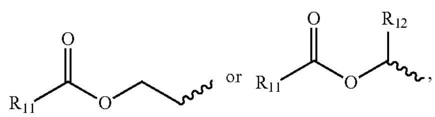

wherein $R_{11}$ and $R_{12}$ independently of each other are selected from linear or branched $C_1$-$C_6$ including -Me, -Et, —Pr, -iPr, -Bu, -iBu, -tBu, pentyl, neopentyl, hexyl; $R_{12}$ is selected from H, -Me, -Et, -iPr;

$R_{13}$, and $R_{14}$ are independently from each other selected from H, F, Cl, Br, I, aryl, straight or branched $C_{1-8}$ alkyl, —$CH_2(CH_2)_p$-aryl, —CH═CH-aryl, $NH_2$, $NO_2$, OH, SH, straight or branched —O—$C_{1-8}$ alkyl, straight or branched —S—$C_{1-8}$ alkyl, straight or branched —NH—$C_{1-8}$ alkyl, —O-aryl, —S-aryl, —NH-aryl, wherein aryl includes aryl having one or more heteroatoms selected from O, N or S, and wherein p is 0 or 1; and $C_{1-8}$ alkyl includes Me, Et, Pr, Bu, pentyl, hexyl, heptyl, octyl-alkyl being linear or branched, or any isomer, tautomer, enantiomer, racemic form or deuterated form thereof, or a pharmaceutically acceptable salt thereof.

In an embodiment of the invention, the compound of formula I has the structure of formula II:

(formula II)

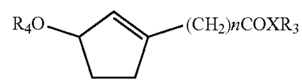

In another embodiment of the invention, the compound of formula I is 3-hydroxycyclopent-1-enecarboxylic acid (HOCPCA), such as (RS)-3-hydroxycyclopent-1-enecarboxylic acid.

In another embodiment said CNS disorder with sleep disturbances is a central hypersomnia, such as narcolepsy.

In another embodiment said CNS disorder with sleep disturbances is a neurodevelopmental disorder with CaMK2a dysfunction such as Angelman syndrome.

Compounds targeting the novel GHB binding site in CaMK2a have never been suggested as drug candidates in Angelman syndrome or other neurodevelopment disorders. The inventors herein demonstrate that the binding site is located in the central organizing (hub) domain of CaMK2a. This is in contrast to other known CaMK2a ligands. The inventors further show that the compounds target CaMK2a in Angelman syndrome mouse brains.

The inventors have, surprisingly, identified small-molecule compounds that bind directly to and regulate CaMK2a function. The compounds according to formula I are the first examples of compounds that target CaMK2a selectively and therefore hold promise in treating central hypersomnias such as narcolepsy and in treating neurodevelopmental disorders with CaMK2a dysfunction such as Angelman syndrome. This suggests the use of compounds of formula I for the treatment of disorders involving CaMK2a dysfunction, e.g. Angelman syndrome. The availability of first-in-class small-molecule compounds with selectivity for CaMK2a, and the fact that these compounds bind in a novel site of the protein, makes this an entirely novel proposition. The proposed uses of the compounds of formula I is clinically relevant and as such has useful applications, as there is currently no targeted medical treatment available for Angelman syndrome patients, including severe sleep disturbances, and as improved treatments of central hypersomnia are needed.

In a second aspect, the present invention provides pharmaceutical compositions for the use in the treatment of central hypersomnias or neurodevelopment disorders in a subject, said composition comprising a compound according to formula I.

In one embodiment the pharmaceutical composition has one dosage of said pharmaceutical composition to comprise from about 0.1 mg to about 1.0 g of said compound of formula I.

In a third aspect, the present invention provides a method for the treatment of central hypersomnias such as narcolepsy or neurodevelopmental disorders such as Angelman Syndrome comprising the administration of an effective amount of a compound of formula I.

In a fourth aspect, the present invention provides a method for the treatment of a disease sensitive to CaMK2a modulation, comprising the administration of an effective amount of a compound of formula I.

BRIEF DESCRIPTION OF THE FIGURES

FIG. 1: Increased $^3$H-HOCPCA binding levels in brain slices from Ube3a (Angelman syndrome) mice, indicating preferred binding to an aberrant form of CaMK2a.

DESCRIPTION

Figure 1:
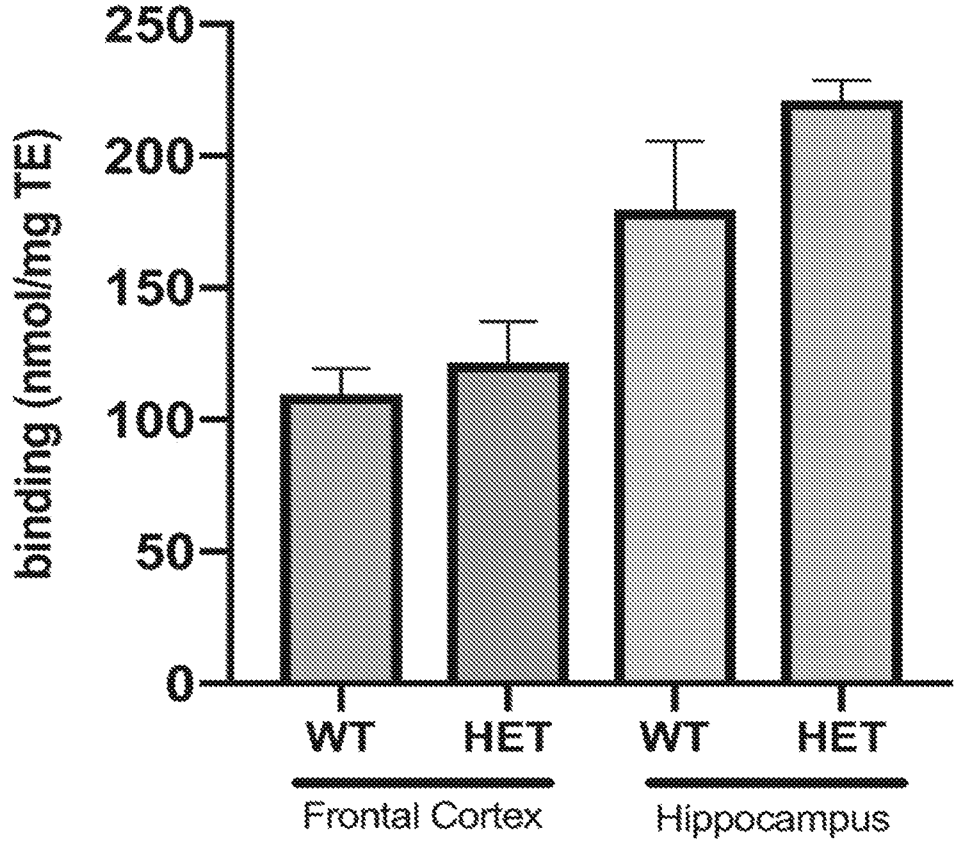
Figure 1:
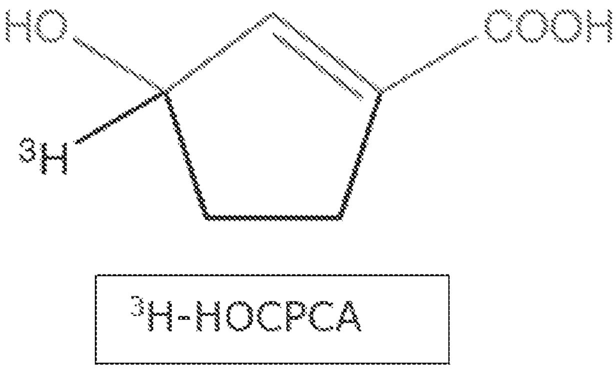

In a first aspect, the present invention provides a compound for use in the treatment of CNS disorders with sleep disturbances such as central hypersomnias or neurodevelopmental disorders such as Angelman Syndrome in a subject, wherein said compound is according to formula I (formula I)

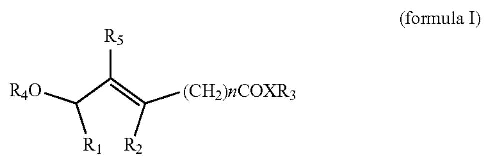

wherein when $R_5$ is H, and $R_1$ and $R_2$ form a ring system, then said compound is selected from the following compounds of formula II or formula IV (formula II)

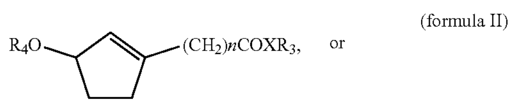

or (formula IV)

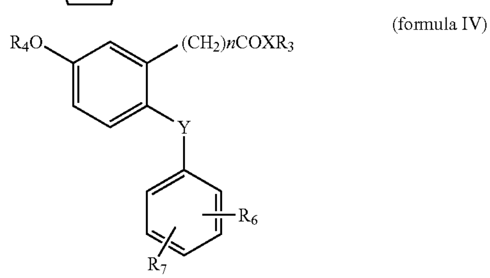

wherein n is 0 or 1;

X is selected from O or NH

Y is NH, O, S, $CH_2$ $R_3$ is selected from H, linear or branched $C_1$-$C_6$-alkyl including -Me, -Et, —Pr, -iPr, -Bu, -tBu, -iBu, pentyl, neopentyl, hexyl, branched henxyl, -benzyl, polyethylenglycolyl (PEG), or a group such as

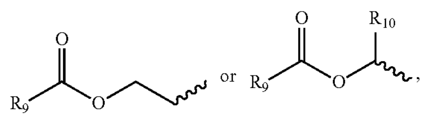

wherein $R_9$ and $R_{10}$ independently of each other are selected from linear or branched $C_1$-$C_6$ including -Me, -Et, —Pr, -iPr, -Bu, -iBu, -tBu, pentyl, neopentyl, hexyl; notably $R_{10}$ is selected from H, -Me, -Et, -iPr;

$R_4$ is selected from H, —C(═O)—$C_1$-$C_6$-alkyl, wherein alkyl is linear or branched including —C(═O)-Me, —C(═O)-Et, —C(═O)—Pr, —C(═O)-iPr, —C(═O)—Bu, —C(═O)-tBu; —C(═O)-benzyl, polyethylenglycolyl (PEG), or a groups such as

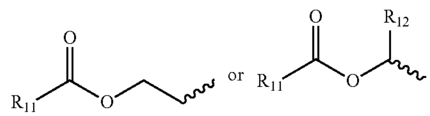

wherein $R_{11}$ and $R_{12}$ independently of each other are selected from linear or branched $C_1$-$C_6$-alkyl including -Me, -Et, —Pr, -iPr, -Bu, -iBu, -tBu, pentyl, neopentyl, hexyl; notably $R_{12}$ is selected from H, -Me, -Et, -iPr; -iBu $R_6$, and $R_7$ are independently from each other selected from H, F, Cl, Br, I, aryl, straight or branched $C_{1-8}$ alkyl, —$CH_2(CH_2)_p$-aryl, —CH═CH-aryl, $NH_2$, $NO_2$, OH, SH, straight or branched —O—$C_{1-8}$ alkyl, straight or branched —S—$C_{1-8}$ alkyl, straight or branched —NH—$C_{1-8}$ alkyl, —O-aryl, —S-aryl, —NH-aryl, wherein aryl includes aryl having one or more heteroatoms selected from O, N or S, and wherein p is 0 or 1; and $C_{1-8}$ alkyl includes Me, Et, Pr, Bu, pentyl, hexyl, heptyl, octyl-alkyl being linear or branched or when $R_2$ is H, and $R_1$ and $R_5$ form a ring system, then said compound has formula III (formula III)

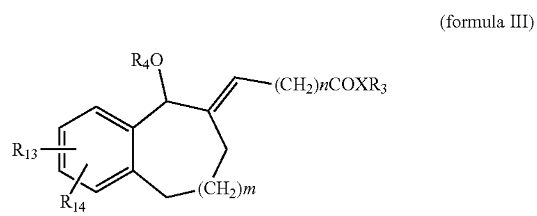

wherein n is 0 or 1;

X is O or NH m is 0 or 1;

$R_3$ is selected from H, linear or branched $C_1$-$C_6$-alkyl including -Me, -Et, —Pr, -iPr, -Bu, -tBu, -iBu, pentyl, isopentyl, neopentyl, hexyl, branched hexyl, -benzyl, polyethylenglycolyl (PEG), or a group such as

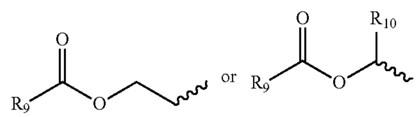

wherein $R_9$ and $R_{10}$ independently of each other are selected from linear or branched $C_1$-$C_6$-alkyl, wherein alkyl is linear or branched including -Me, -Et, —Pr, -iPr, -Bu, -iBu, -tBu, pentyl, neopentyl, hexyl; notably $R_{10}$ is selected from H, -Me, -Et, -iPr;

$R_4$ is selected from H, —C(═O)—$C_1$-$C_6$-alkyl including —C(═O)-Me, —C(═O)-Et, —C(═O)—Pr, —C(═O)-iPr, —C(═O)—Bu, —C(═O)-tBu; —C(═O)-benzyl, polyethylenglycolyl (PEG), or a groups such as

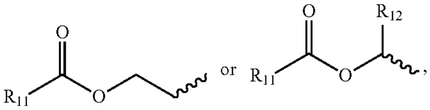

wherein $R_{11}$ and $R_{12}$ independently of each other are selected from linear or branched $C_1$-$C_6$ including -Me, -Et, —Pr, -iPr, -Bu, -iBu, -tBu, pentyl, neopentyl, hexyl; $R_{12}$ is selected from H, -Me, -Et, -iPr;

$R_{13}$, and $R_{14}$ are independently from each other selected from H, F, Cl, Br, I, aryl, straight or branched $C_{1-8}$ alkyl, —$CH_2(CH_2)_p$-aryl, —CH═CH-aryl, $NH_2$, $NO_2$, OH, SH, straight or branched —O—$C_{1-8}$ alkyl, straight or branched —S—$C_{1-8}$ alkyl, straight or branched —NH—$C_{1-8}$ alkyl, —O-aryl, —S-aryl, —NH-aryl, wherein aryl includes aryl having one or more heteroatoms selected from O, N or S, and wherein p is 0 or 1; and $C_{1-8}$ alkyl includes Me, Et, Pr, Bu, pentyl, hexyl, heptyl, octyl-alkyl being linear or branched, or any isomer, tautomer, enantiomer, racemic form or deuterated form thereof, or a pharmaceutically acceptable salt thereof.

Within the scope of the present invention are isomers, tautomers, enantiomers, racemic forms, deuterated forms or mixtures thereof. Thus, e.g. compounds of formula I, which may be present in R or S forms, all such forms are included within the scope of the present invention as well as the racemic mixtures.

The compound of formula I may be prepared as described in PCT/DK2019/050041. A method for the the synthesis of (RS)-3-hydroxycyclopent-1-enecarboxylic acid is also described in Wellendorph et al. J. Pharmacol. Exp. Therap. 2005, 315:346-351.

Based on radioligand binding studies, it has now been found that compounds of formula I bind to a novel site in CaMK2a.

The inventors have identified CaMK2a as the specific high-affinity target for the small molecule GHB and analogues thereof which has structure as formula I. Further studies, as exemplified herein, have demonstrated that GHB analogues bind to a unique site in CaMK2a, more precisely the hub domain, and therefore represent the first small-molecule compounds with selectivity for this very important brain kinase. CaMK2a is involved in important processes in the brain such as synaptic plasticity and learning and memory, and its tight regulation is crucial for normal intellectual development. As the kinase is calcium dependent, it is also centrally involved in conditions of calcium dysregulation such as epilepsy, sleep as well as in ischemia. Mechanistically, CaMK2a is regulated by its own phosphorylation (autophosphorylation), and both mouse models and patients with mutations in these sites exhibit distinct deficits in learning and memory, have seizures and poor sleep regulation (Elgersma et al., Neuron 2002, 36:493-505; Kury et al. Am. J. Human Genetics 2017, 101:768-788).

CaMK2a has never been suggested to be involved in narcolepsy, but the inventors have shown that compounds of formula I targeting CaMK2a are highly efficacious in treating narcolepsy symptoms.

It has been shown by biochemical analysis of a mouse model of AS that CaMK2 activity is reduced and that especially autophosphorylation of the inhibitory sites Thr305 and Thr306 of CaMK2a sites is increased, leading to decreased long-term potentiation (LTP), a hippocampal cellular process correlated with learning and memory/cognition Accordingly, it has been found that the deficits in motor function, seizures, learning disability and LTP in AS mice can be rescued by crossing Ube3a mice with mice harbouring a T305V/306A mutation, alleviating the increased inhibitory phosphorylation level (van Woerden et al. Nature Neurosci 2007, 10, 280-282). The inventors have shown that the binding of compounds of formula I is increased in the hippocampus of mice with Angelman syndrome, suggesting that compounds of formula I are efficacious in treating Angelman syndrome symptoms.

Similarly, increased phosphorylation levels of CaMK2a have been reported in mouse models of Down syndrome, another neurodevelopmental chronic human disease in which mental retardation is the major phenotype. Such mice display learning and behavioural deficits including sleep disturbances (Siarey et al., J Neurochem. 98:1266-1277). CaMK2a dysfunction may also be part of the pathology in other neurodevelopmental disorders characterized by one or more of the symptoms: learning and behavioural deficits, seizure propensity and sleep disturbances. Such disorders include Fragile X, neurofibromatosis type 1, Cri-du-Chat syndromes, succinic semialdehyde dehydrogenase (SSADH) deficiency where GHB levels are abnormal, and Rett syndrome in which CaMK2 dysfunction has also been proposed (Shioda et al., Int J Mol Sci 2018, 19, 20; doi: 10.3390/ijms19010020).

Compounds targeting the novel GHB binding site in CaMK2a have never been suggested as drug candidates in Angelman syndrome or other neurodevelopment disorders. The inventors herein demonstrate that the binding site is located in the central organizing (hub) domain of CaMK2a. The inventors suggest that the compounds may be suitable for treatment of cognitive and or sleep-related symptoms via CaMK2a in Angelman syndrome. For this reason, the compounds of formula targeting CaMK2a are suggested drug candidates for treating Angelman syndrome symptoms and potentially other neurodevelopmental disorders with CaMK2a dysfunction.

Definitions

Autophosphorylation

The term 'autophosphorylation' as used herein refers to the phosphorylation of CaMK2a on residue Thr286, Thr305 or Thr306.

CaMK2a

The term 'CaMK2a' as used herein refers to $Ca^{2+}$/calmodulin-dependent protein kinase type 2 alpha.

Cataplexy

The term 'cataplexy' is a sudden and transient episode of muscle weakness accompanied by full conscious awareness, typically triggered by emotions such as laughing, crying, or terror.

Central Hypersomnia

Disorders of excessive daytime sleepiness related to the central nervous system, i.e., the brain. These disorders share in common the predominant symptom of daytime sleepiness. Various types of central hypersomnias exist, including idiopathic hypersomnia, recurrent hypersomnia such as Klein-Levin syndrome, and narcolepsy.

In an embodiment, the compounds of formula I are contemplated to have beneficial effects in preventing and/or alleviating central hypersomnias and cataplexies. Central hypersomnias include idiopathic hypersomnia, recurrent hypersomnia such as Klein-Levin syndrome and narcolepsy including with cataplexy (narcolepsy type 1; narcolepsy-cataplexy syndrome; NRCLP1; narcolepsy with low hypocretin) and narcolepsy without cataplexy (narcolepsy type 2; narcolepsy with normal hypocretin).

Narcolepsy Type 1 and Type 2 are sleep disorders characterized by excessive daytime sleepiness and narcolepsy Type 1 is further characterized by cataplexy. Cataplexy is characterized by sudden loss of muscle tone. The duration of cataplexy is usually short, ranging from a few seconds to several minutes and recovery is immediate and complete. The loss of muscle tone varies in severity and ranges from a mild sensation of weakness with head drop, facial sagging, jaw drop, slurred speech and buckling of the knees to complete postural collapse, with a fall to the ground. Cataplexy is usually precipitated by emotion that usually has a pleasant or exciting component, such as laughter, elation, pride, anger or surprise.

Besides excessive daytime sleepiness and cataplexy (in narcolepsy type 1), individuals affected by narcolepsy often present symptoms such as sleep fragmentation, abnormal rapid eye movement sleep, nocturnal sleep disruption, paralysis during sleep onset or during awakening; and/or hypnagogic hallucinations. Similar symptoms are shown also by individuals affected by Narcolepsy Due to Medical Condition (NDMC), a group of disorders also known as secondary or symptomatic narcolepsy.

Examples of medical conditions causing narcolepsy symptoms including cataplexy are: tumors, ischemic stroke, sarcoidosis, arteriovenous malformations affecting the hypothalamus, multiple sclerosis plaques impairing the hypothalamus, paraneoplastic syndrome antt-Ma2 antibodies, Neimann-Pick type C disease or Coffin-Lowry syndrome. Examples of medical conditions commonly causing narcolepsy symptoms without cataplexy are: head trauma, myotonic dystrophy, Prader-Willi syndrome, Parkinson's disease or multisystem atrophy.

Cataplexy is a hallmark of narcolepsy but may also be associated with specific lesions located primarily in the lateral and posterior hypothalamus, as e.g. tumors (astrocytoma, glioblastoma, glioma, craniopharyngioma and subependynoma) and arterio-venous malformations. Conditions in which cataplexy can be seen include ischemic events, multiple sclerosis, head injury, paraneoplastic syndromes, and infections, such as encephalitis. Cataplexy may occur transiently or permanently due to lesions of the hypothalamus that were caused by surgery, especially in difficult tumor resections. In infancy, cataplexy can be seen in association with other neurological syndromes such as Niemann-Pick type C disease.

GHB Analogues

The term 'GHB analogue' as used herein refers to compounds that share a common GHB-related structure and bind to a unique site in CaMK2a.

Neurodevelopmental Disorders Involving CaMK2a Dysfunction

This term refers to human diseases, mostly of genetic origin, in which there is a component of CaMK2a dysfunction. The disorders share a common symptomology of learning and behavioural deficits, increased seizure propensity and sleep disturbances. Included in this definition is disease-causing CaMK2 mutations, Angelman syndrome, Down syndrome, Fragile X, neurofibromatosis type 1, Cri-du-Chat syndromes, SSADH deficiency, and Rett syndrome.

Pharmaceutical Compositions Comprising a Compound of the Invention:

The present invention also provides a pharmaceutical composition comprising the compound of the invention together with one or more pharmaceutically acceptable diluents or carriers.

The compound of the invention or a formulation thereof may be administered by any conventional method for example but without limitation it may be administered parenterally, orally, topically (including buccal, sublingual or transdermal), via a medical device (e.g. a stent), by inhalation or via injection (subcutaneous or intramuscular). The treatment may consist of a single dose or a plurality of doses over a period of time. The treatment may be by administration once daily, twice daily, three times daily, four times daily etc. The treatment may also be by continuous administration such as e.g. administration intravenous by drop.

Whilst it is possible for the compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compound of the invention will normally be administered intravenously, orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

For example, the compound of the invention can also be administered orally, buccally or sublingually in the form of tablets, capsules, ovules, elixirs, solutions or suspensions, which may contain flavouring or colouring agents, for immediate-, delayed- or con-trolled-release applications.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Solutions or suspensions of the compound of the invention suitable for oral administration may also contain excipients e.g. N,N-dimethylacetamide, dispersants e.g. poly-sorbate 80, surfactants, and solubilisers, e.g. polyethylene glycol, Phosal 50 PG (which consists of phosphatidylcholine, soya-fatty acids, ethanol, mono/diglycerides, propylene glycol and ascorbyl palmitate). The formulations according to present invention may also be in the form of emulsions, wherein a compound according to formula I may be present in an aqueous oil emulsion. The oil may be any oil-like substance such as e.g. soy bean oil or safflower oil, medium chain triglycieride (MCT-oil) such as e.g. coconut oil, palm oil etc or combinations thereof.

Tablets may contain excipients such as microcrystalline cellulose, lactose (e.g. lactose monohydrate or lactose anyhydrous), sodium citrate, calcium carbonate, dibasic calcium phosphate and glycine, butylated hydroxytoluene (E321), crospovidone, hypromellose, disintegrants such as starch (preferably corn, potato or tapioca starch), sodium starch glycollate, croscarmellose sodium, and certain complex silicates, and granulation binders such as polyvinylpyrrolidone, hydroxypropylmethylcellulose (HPMC), hydroxy-propylcellulose (HPC), macrogol 8000, sucrose, gelatin and acacia. Additionally, lubricating agents such as magnesium stearate, stearic acid, glyceryl behenate and talc may be included.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either colloidal, suspended or dissolved in the vehicle. In preparing solutions the active ingredient can be dissolved in water for injection and filter sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Pharmaceutical compositions of the present invention suitable for injectable use in-elude sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

It should be understood that in addition to the ingredients particularly mentioned above the formulations of this invention may include other agents conventional in the art having regard to the type of formulation in question, for example those suitable for oral administration may include flavouring agents. A person skilled in the art will know how to choose a suitable formulation and how to prepare it (see eg Remington's Pharmaceutical Sciences 18 Ed. or later). A person skilled in the art will also know how to choose a suitable administration route and dosage.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

All % values mentioned herein are % w/w unless the context requires otherwise.

The following embodiments illustrate the present invention:

1. A compound for use in the treatment of a CNS disorder with sleep disturbances in a subject, wherein said compound is according to formula I (formula I)

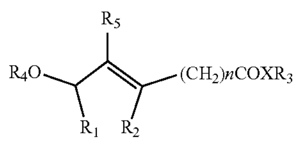

wherein when $R_5$ is H, and $R_1$ and $R_2$ form a ring system, then said compound is selected from the following compounds of formula II or formula IV (formula II)

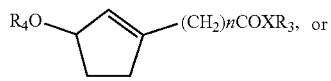

or (formula IV)

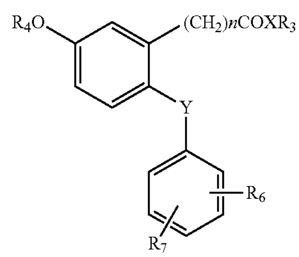

wherein n is 0 or 1;

X is selected from O or NH

Y is NH, O, S, $CH_2$ $R_3$ is selected from H, linear or branched $C_1$-$C_6$-alkyl including -Me, -Et, —Pr, -iPr, -Bu, -tBu, -iBu, pentyl, neopentyl, hexyl, branched henxyl, -benzyl, polyethylenglycolyl (PEG), or a group such as

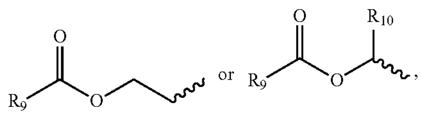

wherein $R_9$ and $R_{10}$ independently of each other are selected from linear or branched $C_1$-$C_6$ including -Me, -Et, —Pr, -iPr, -Bu, -iBu, -tBu, pentyl, neopentyl, hexyl; notably $R_{10}$ is selected from H, -Me, -Et, -iPr;

$R_4$ is selected from H, —C(═O)—$C_1$-$C_6$-alkyl, wherein alkyl is linear or branched including —C(═O)-Me, —C(═O)-Et, —C(═O)—Pr, —C(═O)-iPr, —C(═O)—Bu, —C(═O)-tBu; —C(═O)-benzyl, polyethylenglycolyl (PEG), or a groups such as

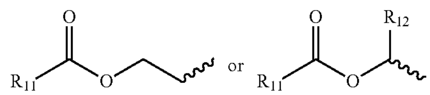

wherein $R_{11}$ and $R_{12}$ independently of each other are selected from linear or branched $C_1$-$C_6$-alkyl including -Me, -Et, —Pr, -iPr, -Bu, -iBu, -tBu, pentyl, neopentyl, hexyl; notably $R_{12}$ is selected from H, -Me, -Et, -iPr; -iBu $R_6$, and $R_7$ are independently from each other selected from H, F, Cl, Br, I, aryl, straight or branched $C_{1-8}$ alkyl, —$CH_2(CH_2)_p$-aryl, —CH═CH-aryl, $NH_2$, $NO_2$, OH, SH, straight or branched —O—$C_{1-8}$ alkyl, straight or branched —S—$C_{1-8}$ alkyl, straight or branched —NH—$C_{1-8}$ alkyl, —O-aryl, —S-aryl, —NH-aryl, wherein aryl includes aryl having one or more heteroatoms selected from O, N or S, and wherein p is 0 or 1; and $C_{1-8}$ alkyl includes Me, Et, Pr, Bu, pentyl, hexyl, heptyl, octyl-alkyl being linear or branched or when $R_2$ is H, and $R_1$ and $R_5$ form a ring system, then said compound has formula III (formula III)

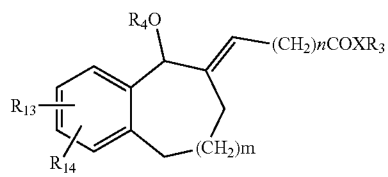

wherein n is 0 or 1;

X is O or NH m is 0 or 1;

$R_3$ is selected from H, linear or branched $C_1$-$C_6$-alkyl including -Me, -Et, —Pr, -iPr, -Bu, -tBu, -iBu, pentyl, isopentyl, neopentyl, hexyl, branched hexyl, -benzyl, polyethylenglycolyl (PEG), or a group such as

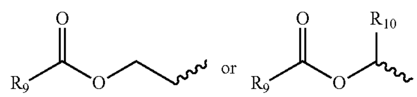

wherein $R_9$ and $R_{10}$ independently of each other are selected from linear or branched $C_1$-$C_6$-alkyl, wherein alkyl is linear or branched including -Me, -Et, —Pr, -iPr, -Bu, -iBu, -tBu, pentyl, neopentyl, hexyl; notably $R_{10}$ is selected from H, -Me, -Et, -iPr;

$R_4$ is selected from H, —C(═O)—$C_1$-$C_6$-alkyl including —C(═O)-Me, —C(═O)-Et, —C(═O)—Pr, —C(═O)-iPr, —C(═O)—Bu, —C(═O)-tBu; —C(═O)-benzyl, polyethylenglycolyl (PEG), or a groups such as

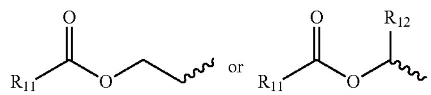

wherein $R_{11}$ and $R_{12}$ independently of each other are selected from linear or branched $C_1$-$C_6$ including -Me, -Et, —Pr, -iPr, -Bu, -iBu, -tBu, pentyl, neopentyl, hexyl; $R_{12}$ is selected from H, -Me, -Et, -iPr;

$R_{13}$, and $R_{14}$ are independently from each other selected from H, F, Cl, Br, I, aryl, straight or branched $C_{1-8}$ alkyl, —$CH_2(CH_2)_p$-aryl, —CH═CH-aryl, $NH_2$, $NO_2$, OH, SH, straight or branched —O—$C_{1-8}$ alkyl, straight or branched —S—$C_{1-8}$ alkyl, straight or branched —NH—$C_{1-8}$ alkyl, —O-aryl, —S-aryl, —NH-aryl, wherein aryl includes aryl having one or more heteroatoms selected from O, N or S, and wherein p is 0 or 1; and $C_{1-8}$ alkyl includes Me, Et, Pr, Bu, pentyl, hexyl, heptyl, octyl-alkyl being linear or branched, or any isomer, tautomer, enantiomer, racemic form or deuterated form thereof, or a pharmaceutically acceptable salt thereof.

2. A compound according to embodiment 1 having formula II.

3. A compound according to embodiment 1 having formula II or III, and wherein n is 0.

4. The compound according to any of the preceding embodiments, wherein both $R_3$ and $R_4$ are H.

5. The compound according to any of the preceding embodiments which is selected from

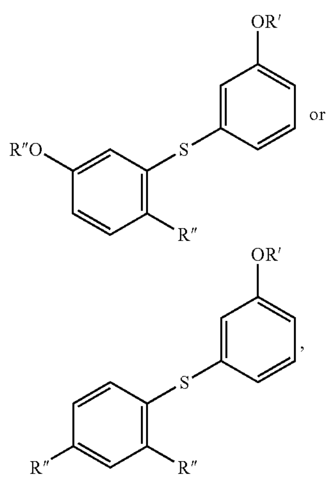

or a pharmaceutically acceptable salt thereof, wherein R' is COOH, R" is H and R'" is $OCH_3$, or wherein R' is COOH, R" is $CH_3$ and R'" is OH.

6. The compound according to any of the preceding embodiments, which is selected from

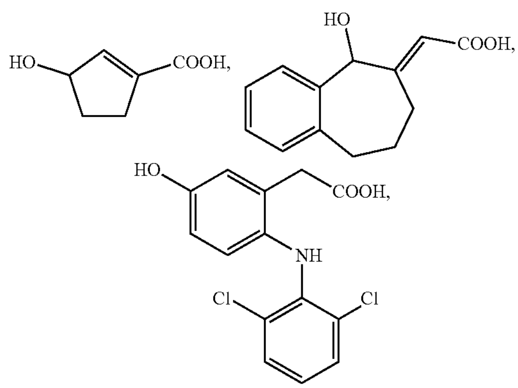

or a pharmaceutically acceptable salt thereof.

7. The compound according to embodiment 6, which is

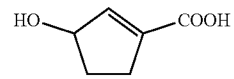

or a pharmaceutically acceptable salt thereof.

8. The compound according to embodiment 7, which is the sodium salt or the potassium salt.

9. The compound according to any of embodiments 1-8, which is in a crystalline state.

10. The compound according to any of embodiments 1-9, wherein said compound is to be administered to said subject in a dose from about 0.01 mg/kg to about 100 mg/kg.

11. The compound according to any of the preceding embodiments, wherein said compound is to be administered to said subject in a dose from about 0.1 mg/kg to about 10 mg/kg.

12. The compound according to any of the preceding embodiments, wherein from about 0.1 mg to about 1.0 g of said compound is to be administered to said subject.

13. The compound according to embodiment 12, wherein from about 1 mg to about 1000 mg of said compound is to be administered to said subject.

14. The compound according to any of the preceding embodiments, wherein said CNS disorder with sleep disturbances is a central hypersomnia.

15. The compound according to embodiment 14, wherein said central hypersomnia is selected from the group consisting of idiopathic hypersomnia, recurrent hypersomnia, Klein-Levin syndrome and narcolepsy 16. The compound according to any of the preceding embodiments, wherein said CNS disorder with sleep disturbances is narcolepsy.

17. The compound according to any of the preceding embodiments, wherein the use reduces at least one of said subject's symptoms of narcolepsy.

18. The compound according to embodiment 17, wherein said symptom is selected from excessive daytime sleepiness, cataplexy, abnormal REM sleep, sleep paralysis or night-time wakefulness.

19. The compound according to any of the preceding embodiments, wherein said treatment of narcolepsy is the treatment of narcolepsy with cataplexy (Type 1 narcolepsy).

20. The compound according to any one of embodiments 1-18, wherein said treatment of narcolepsy is the treatment of narcolepsy without cataplexy (Type 2 narcolepsy)

21. The compound according to any one of embodiments 1-18, wherein said treatment of narcolepsy is the treatment of secondary narcolepsy.

22. The compound according to any of embodiments 1-13, wherein said CNS disorder is a neurodevelopmental disorder.

23. The compound according to any of embodiments 1-13, wherein said CNS disorder is caused by a genetic CaMK2 mutation.

24. The compound according to any of embodiments 1-13, wherein said CNS disorder is Angelman syndrome or Downs syndrome.

25. The compound according to any of the preceding embodiments, wherein the use further comprises the administration of a CNS stimulant, an antidepressant or a GABA receptor agonist.
26. The compound according to embodiment 25, wherein said CNS stimulant is selected from the group consisting of modafinil, armodafinil, methylphenidate, amphetamine, dextroamphetamine, methamphetamine, phentermine, phendimetrazine, diethylpropion, lisdexamfetamine, benzphetamine, atomoxetine, caffeine and ephedrine.
27. The compound according to embodiment 25, wherein said antidepressant is selected from the group consisting of serotonin and noradrenaline reuptake inhibitors (SNRIs), selective serotonin reuptake inhibitors (SSRIs), tricyclic antidepressants (TCAs), monoamine oxidase inhibitors (MAOIs) and noradrenaline and specific serotoninergic antidepressants (NASSAs).
28. The compound according to embodiment 25, wherein said GABA receptor agonist is selected from the group consisting of sodium oxybate, baclofen, phenibut, and gaboxadol.
29 A pharmaceutical composition for the use in the treatment of a CNS disorder with sleep disturbances in a subject, comprising a compound according to any of embodiments 1-29.
30. The pharmaceutical composition according to embodiment 29, wherein said CNS disorder with sleep disturbances is a central hypersomnia.
31. The pharmaceutical composition according to embodiment 30, wherein said central hypersomnia is narcolepsy.
32. The pharmaceutical composition according to embodiment 29, wherein said CNS disorder with sleep disturbances is a neurodevelopmental disorder.
33. The pharmaceutical composition according to embodiment 32, wherein said neurodevelopmental disorder is Angelman syndrome or Downs syndrome or caused by genetic CaMK2 mutations.
34. The pharmaceutical composition according to any of embodiments 28-33, wherein one dosage of said pharmaceutical composition comprises from about 0.1 mg to about 5.0 g of said compound.
35. The pharmaceutical composition according to embodiment 34, wherein one dosage of said pharmaceutical composition comprises from about 10 mg to about 1.0 g of said compound.
36. The pharmaceutical composition according to embodiment 34, wherein one dosage of said pharmaceutical composition comprises from about 50 mg to about 500 mg of said compound.
37. The pharmaceutical composition according to embodiment 34, wherein one dosage of said pharmaceutical composition comprises from about 250 mg to about 5.0 g of said compound.
38. The pharmaceutical composition according to embodiment 34, wherein one dosage of said pharmaceutical composition comprises from about 0.5 mg to about 50 mg of said compound.
30. A method for the treatment of a CNS disorder with sleep disturbances, comprising the administration of an effective amount of a compound as defined in any of embodiments 1-28.
40. The method according to embodiment 39, wherein said CNS disorder with sleep disturbances is a central hypersomnia.
41. The method according to embodiment 40, wherein said central hypersomnia is narcolepsy.
42. The method according to any of embodiments 40-41, wherein said central hypersomnia is selected from the group consisting of Type 1 narcolepsy, Type 2 narcolepsy and secondary narcolepsy.
43. The method according to embodiment 39, wherein said CNS disorder with sleep disturbances is a neurodevelopmental disorder.
44. The method according to embodiment 43, wherein said neurodevelopmental disorder is Angelman syndrome or Downs syndrome.
45. The method according to any of embodiments 39-44, wherein the method further comprises the administration of a CNS stimulant, an antidepressant, a $GABA_A$ receptor agonist or a $GABA_B$ receptor agonist.
46. The method according to embodiment 45, wherein said CNS stimulant is selected from the group consisting of modafinil, armodafinil, methylphenidate, amphetamine, dextroamphetamine, methamphetamine, phentermine, phendimetrazine, diethylpropion, lisdexamfetamine, benzphetamine, atomoxetine, caffeine and ephedrine.
47. The method according to embodiment 45, wherein said antidepressant is selected from the group consisting of serotonin and noradrenaline reuptake inhibitors (SNRIs), selective serotonin reuptake inhibitors (SSRIs), tricyclic antidepressants (TCAs), monoamine oxidase inhibitors (MAOIs) and noradrenaline and specific serotoninergic antidepressants (NASSAs).
48. The method according to embodiment 45, wherein said $GABA_B$ receptor agonist is selected from the group consisting of sodium oxybate, baclofen and phenibut.
49. The method according to embodiment 45, wherein said $GABA_A$ receptor agonist is gaboxadol.
50. A method for the treatment of a disease sensitive to CaMK2a modulation, comprising the administration of an effective amount of a compound as defined in any of embodiments 1-28.

EXAMPLES

Materials and Methods

Mouse Brain $^3$H-HOCPCA Autoradiography

According to previously published protocols, mouse brains from either (Ube3a$^{m-/p+}$) or wildtype mice, were dissected, sliced on a cryostat, mounted on glass slides, and $^3$H-HOCPCA autoradiography performed as described (Griem-Krey et al. 2019, J Vis Exp Ther, 145:e58879). The binding protocol was performed with 1 nM $^3$H-HOCPCA radioligand prepared in-house (Vogensen et al., 2013, J Med Chem 56:8201-8205) and using 1 mM GHB for non-specific binding. The buffer was 50 mM potassium phosphate, pH 6.0. Washed and dried sections were exposed to a phosphor imaging plate (Science Imaging Scandinavia AB, Nacka, Sweden) for 3 days together with a $^3$H microscale to convert to tissue equivalents (TE). The imaging plate was scanned on a CR35 Bio Scanner (DQrr Medical). Subsequently, densitometric analysis was performed using Image J (NIH) and data (nmol/mg TE) further analyzed with GraphPad Prism 7, GraphPad Prism Software, San Diego, CA, USA.

$^3$H-HOCPCA Binding to Recombinant CaMK2a Expressed in HEK293T Cells

HEK293T cells were cultured using standard conditions, using Dulbecco's modified Eagle Medium with GlutaMax, 10% fetal bovine serum and 1% penicillin-streptomycin, and incubated at 37° C. in a humidified atmosphere of 95% $O_2$ and 5% $CO_2$. Site-directed mutagenesis was done using point mutations and performed by GenScript USA Inc. Cells were transfected with wild-type or mutated cmyc-tagged rat CaMK2a (Origene construct RR201121), using polyethimine, linear, MW 25000 (Polysciences Inc., Warrington, PA, USA). Whole cell homogenates were prepared 48 hr post-transfection by washing the cells with ice-cold 1×PBS and harvesting by scraping. Cells were collected and centrifuged for 10 min at 1000×g. Cell pellets were resuspended in ice-cold 1×PBS and homogenized using 2×1 mm zirkonium beads in a bullet blender for 20 s at max speed (NextAdvance, NY, USA). Homogenates were cleared by centrifugation (10 min, 4° C., 14.000×25 g). Protein concentration was determined using the Bradford protein assay. 150-200 μg protein was incubated with 5 nM $^3$H-HOCPCA (Vogensen et al., 2013, J Med Chem 56:8201-8205) and test compound in 1 ml total volume for 1 hr at 0-4° C. Nonspecific binding was determined with 1-10 mM GHB. Proteins were then precipitated by addition of ice-cold acetone (4× of the assay volume), vortexing and incubation at −20° C. for 1 hr. Proteins were filtered 30 rapidly through GF/C unifilters (Whatman) and washed using a 48-well harvester. The dried filters were added scintillation liquid and radioactivity measured on a Tricarb 2100 Scintillation counter (Packard). Data analysis was performed using GraphPad Prism 7, GraphPad Prism Software, San Diego, CA, USA.

Total expression levels of CaMK2a were assessed by Western blot with anti-myc-Alexa488 (MA1980-A488, ThermoFisher Scientific).

Example 1—the Specific CaMK2a Radioligand $^3$H-HOCPCA Displays Increased Binding to Angelman Syndrome Brains Angelman syndrome mice (Ube3a$^{m-/p+}$, HET) brain slices were compared to control mice (WT) using $^3$H-HOCPCA autoradiography. The difference observed is most pronounced in the hippocampus where CaMK2a is highly expressed. The data highlights that GHB-related compounds may have effects in Angelman syndrome via binding to the form of CaMK2a that accumulates in this disorder (FIG. 1).

Figure 2:
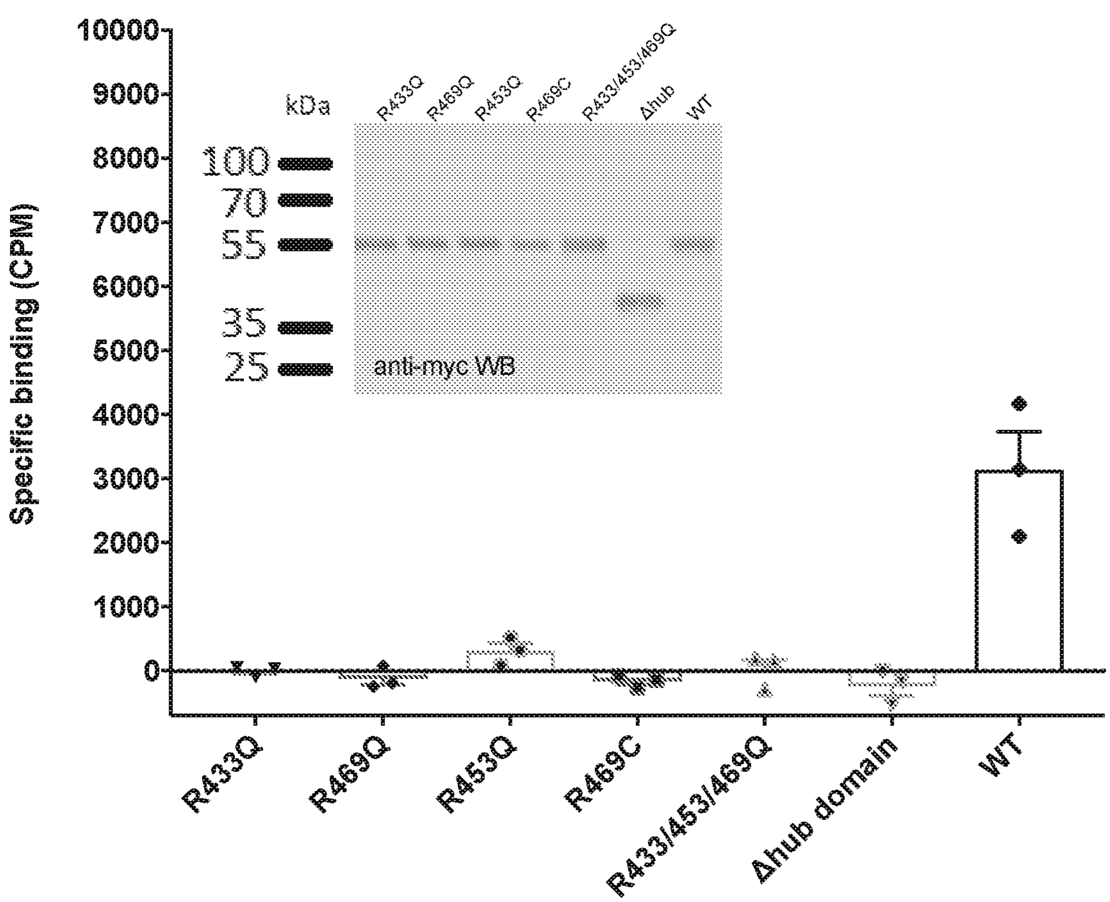
FIG. 2: Abolished 3H-HOCPCA in mutations of the CaMK2a hub domain, showing the location of the binding site.

Example 2—Binding Site of $^3$H-HOCPCA is Confined to the Hub Domain Cavity of CaMK2a as Show by Mutagenesis Analysis CaMK2a constructs with the specific mutations Arg433Gln, Arg453Gln and Arg469Cys, Arg469Gln, or the triple mutant or a construct with the hub deleted (delta hub), were expressed in HEK cells and whole cell homogenates exposed to in an in-house $^3$H-HOCPCA filtration binding assay. Compared to wild-type, each of the three mutations completely abolished binding although expression was confirmed by WB (FIG. 2).

Example 3—Assessment of $^3$H-HOCPCA Binding Levels in Narcolepsy

Mouse brain slices from a narcolepsy mouse model are compared to control mice (WT) using $^3$H-HOCPCA autoradiography using methods as described in example 1.

Example 4—Evaluation of Locomotor Activity of Selected Compounds in Mice

To determine locomotor effects (e.g. sedation or hyperactivity) compounds are assessed after systemic administration to mice. Mice (typically n=5-8) are administered a compound of Formula I and vehicle controls, and placed in transparent cages (L: 37 cm×W: 21 cm×H: 15 cm). Locomotor activity are then measured via a camera mounted above the arena. Mice are recorded for about 120 min and data collected in 5-min intervals.

Figure 3:
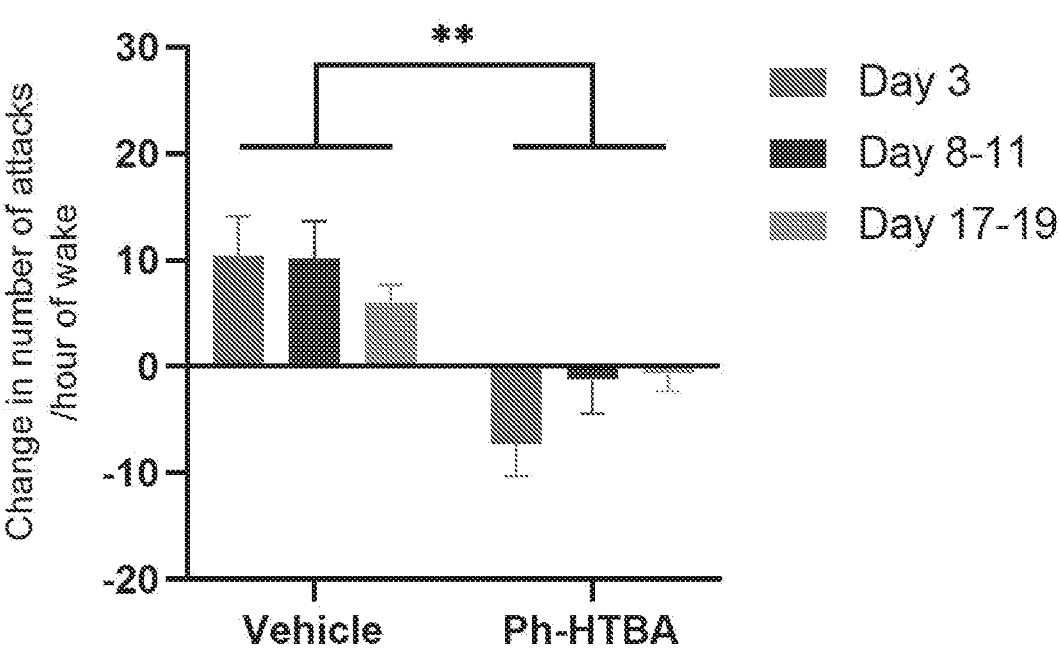
FIG. 3: Evaluation of a selected compound in the DTA mouse model of narcolepsy

Example 5—Evaluation of a Selected Compound in the DTA Mouse Model of Narcolepsy Using the DTA narcolepsy mouse model we are determining changes in sleepwake EEG/EMG patterns (including cataplexy) at different time points (1 day to 3 weeks) under the influence of a compound of Formula I (Ph-HTBA). After drug cessation, EEG/EMG changes are then further mapped for up to 4 weeks. Under anesthesia with isoflurane (2% to 2.5% in O2) electrodes are placed in the scull and neck muscles of the mice. After 5-10 days recovery the electrodes are connected to a recording system, and EEG/EMG signals are recorded with synchronised video recordings. From the data, sleep/wake parameters and cataplexy episodes are scored and calculated FIG. 3). The treatment has an overall statistical significant effect in a two-way ANOVA model, p=0.0017, n=5-6.

Figure 4:
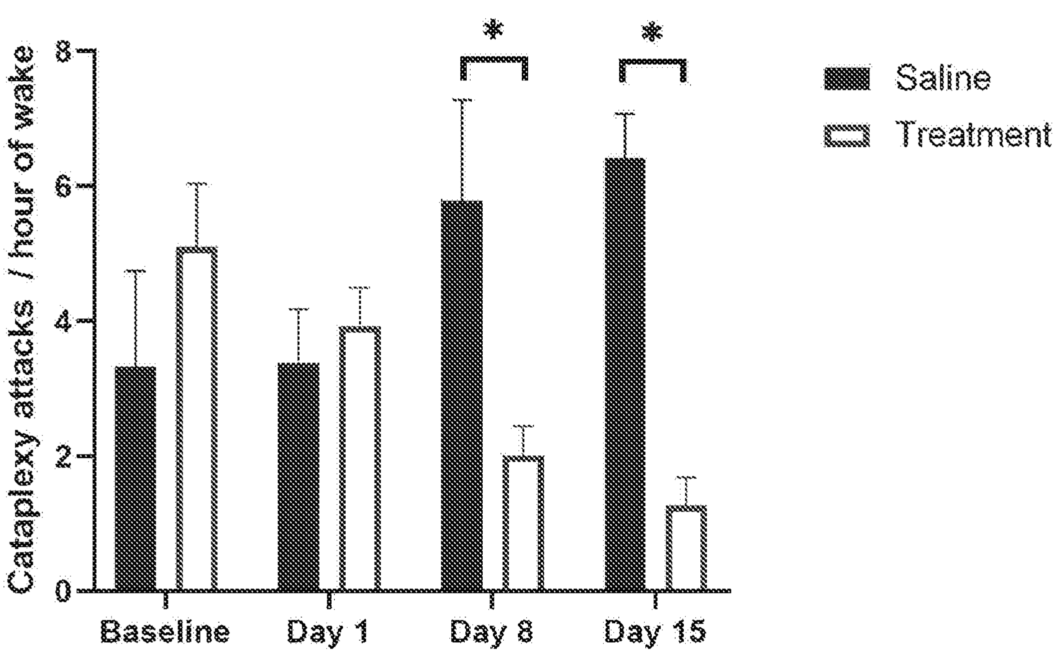
FIGS. 4-5: Evaluation of a selected compound in the Hcrt-KO mouse model of narcolepsy
Figure 5:
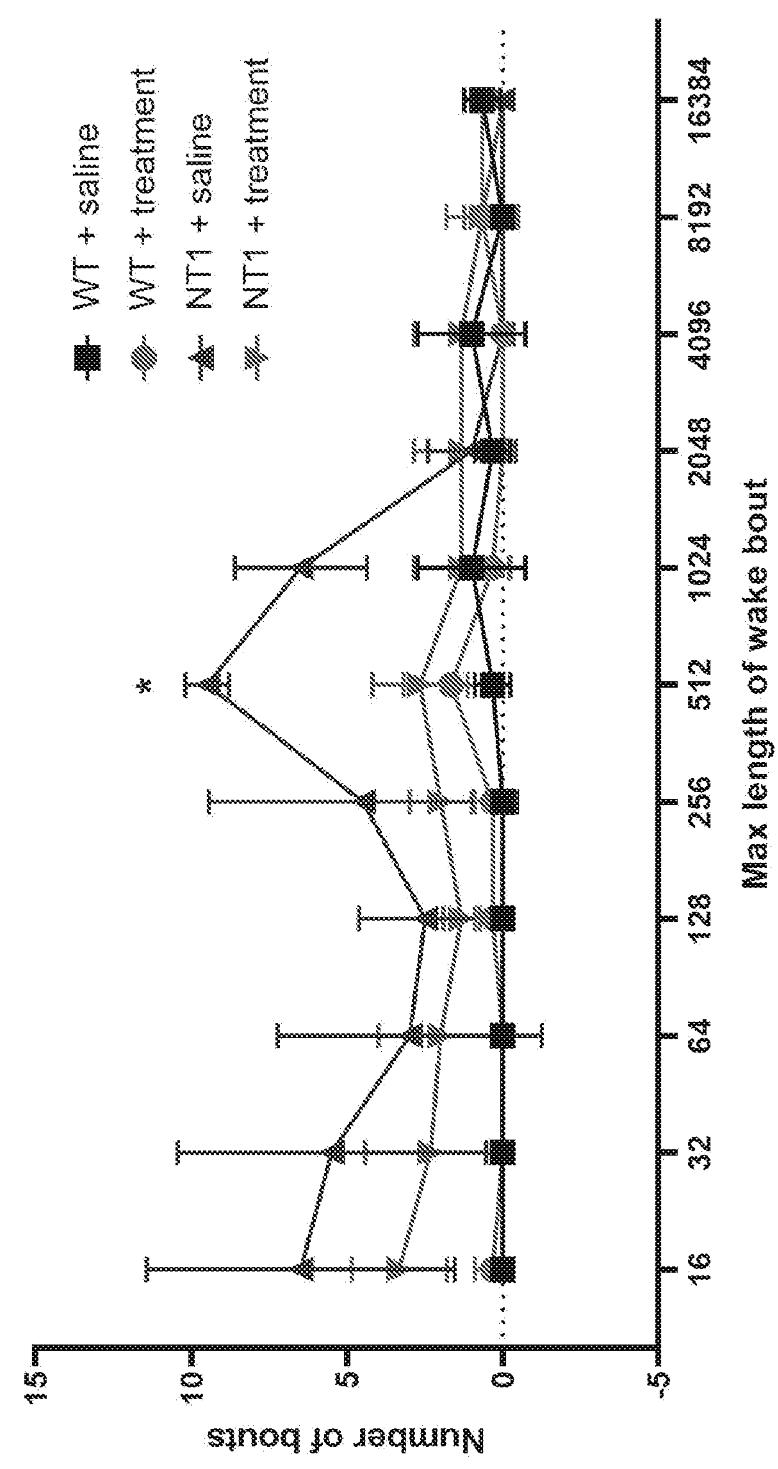

Example 6—Evaluation of a Selected Compound in a Hypocretin Knock-Out Mouse Model of Narcolepsy Using the hypocretin knock-out mouse model we determine changes in sleep-wake EEG/EMG patterns (including cataplexy) at different time points (1 day to 3 weeks) under the influence of a compound (HOCPCA) of Formula I. After drug cessation, EEG/EMG changes are then further mapped for up to 4 weeks. Under anesthesia with isoflurane (2% to 2.5% in O2) electrodes are placed in the scull and neck muscles of the mice. After 5-10 days recovery the electrodes are connected to a recording system, and EEG/EMG signals are recorded with synchronised video recordings. From the data, sleep/wake parameters and cataplexy episodes are scored and calculated (FIG. 4-5). The treatment decreases cataplexy significantly on day 8, p=0.044 and day 15 p=0.010 (mixed-effects model with post hoc Sidak comparisons, FIG. 4). The treatment further stabilizes wakefulness with a significant decrease of medium long wake bouts in the narcolepsy model p=0.01, two-way ANOVA with post hoc Dunnett comparison.

The invention claimed is:

1. A method of treating a CNS disorder with sleep disturbances in a subject, said method comprising administering to said subject a compound having a formula selected from formula II (formula II)

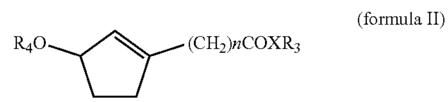

wherein n is 0 or 1;

X is O or NH $R_3$ is H, linear or branched $C_1$-$C_6$-alkyl-benzyl, polyethyleneglycolyl (PEG),

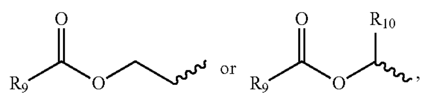

wherein $R_9$ is linear or branched $C_1$-$C_6$ alkyl;

$R_{10}$ is H, linear or branched $C_1$-$C_6$ alkyl;

$R_4$ is H, —C(═O)—$C_1$-$C_6$-alkyl, wherein alkyl is linear or branched; —C(═O)-benzyl, polyethyleneglycolyl (PEG),

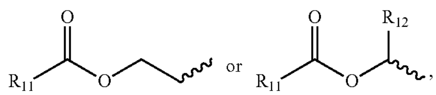

wherein $R_{11}$ is linear or branched $C_1$-$C_6$-alkyl;

$R_{12}$ is H, linear or branched $C_1$-$C_6$ alkyl;

or formula III (formula III)

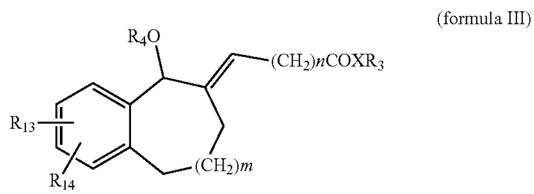

wherein n is 0 or 1;

X is O or NH m is 0 or 1;

$R_3$ is H, linear or branched $C_1$-$C_6$-alkyl, -benzyl, polyethyleneglycolyl (PEG),

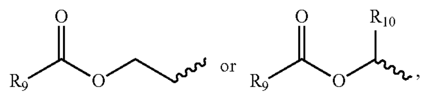

wherein $R_9$ linear or branched $C_1$-$C_6$-alkyl, wherein alkyl is linear or branched;

$R_{10}$ is H, linear or branched $C_1$-$C_6$-alkyl;

$R_4$ is H, —C(═O)—$C_1$-$C_6$-alkyl; —C(═O)-benzyl, polyethyleneglycolyl (PEG)

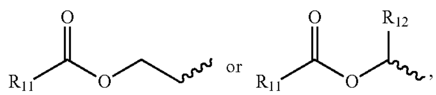

wherein $R_{11}$ is linear or branched $C_1$-$C_6$ alkyl;

$R_{12}$ is H, linear or branched $C_1$-$C_6$ alkyl;

$R_{13}$, and $R_{14}$ are independently from each other H, F, Cl, Br, I, aryl, straight or branched $C_{1-8}$ alkyl, —$CH_2(CH_2)_p$-aryl, —CH═CH-aryl, $NH_2$, $NO_2$, OH, SH, straight or branched —O—$C_{1-8}$ alkyl, straight or branched —S—$C_{1-8}$ alkyl, straight or branched —NH—$C_{1-8}$ alkyl, —O-aryl, —S-aryl, —NH-aryl, wherein aryl includes aryl having one or more heteroatoms that are O, N or S, and wherein p is 0 or 1, or any tautomer, enantiomer, racemic form or deuterated form thereof, or a pharmaceutically acceptable salt thereof, wherein the CNS disorder with sleep disturbances is a central hypersomnia or a neurodevelopmental disorder.

2. The method according to claim 1, wherein the compound has the structure of formula II.

3. The method according to claim 1, wherein both $R_3$ and $R_4$ are H.

4. The method according to claim 3, wherein the compound is

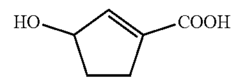

or any tautomer, enantiomer, racemic form or deuterated form thereof, or a pharmaceutically acceptable salt thereof.

5. The method according to claim 3, wherein said compound is in a pharmaceutical composition.

6. The method according to claim 1, wherein said compound is in a pharmaceutical composition.

7. The method according to claim 1, wherein the method further comprises the administering of a CNS stimulant, an antidepressant or a GABA receptor agonist to said subject.

8. The method according to claim 1, wherein said central hypersomnia is idiopathic hypersomnia or recurrent hypersomnia.

9. The method according to claim 8, wherein said recurrent hypersomnia is Klein-Levin syndrome.

10. The method according to claim 1, wherein said central hypersomnia is narcolepsy.

11. The method according to claim 10, wherein the administration of the compound to the subject reduces at least one of said subject's symptoms of narcolepsy.

12. The method according to claim 1, wherein said neurodevelopmental disorder is Angelman syndrome.

13. The method according to claim 1, wherein said neurodevelopmental disorder is Down syndrome, Fragile X, Cri-du-Chat syndromes, succinic semialdehyde dehydrogenase (SSADH) deficiency, neurofibromatosis type 1, Rett syndrome, or Angelman syndrome.

* * * * *